United States Patent [19]

Lembach

[11] Patent Number: 4,720,385

[45] Date of Patent: Jan. 19, 1988

[54] PROTEIN COMPOSITIONS SUBSTANTIALLY FREE FROM INFECTIOUS AGENTS

[75] Inventor: Kenneth J. Lembach, Danville, Calif.

[73] Assignee: Miles Laboratories, Inc., Elkhart, Ind.

[21] Appl. No.: 736,197

[22] Filed: May 20, 1985

Related U.S. Application Data

[63] Continuation-in-part of Ser. No. 480,056, Mar. 29, 1983, Pat. No. 4,534,972.

[51] Int. Cl.$^4$ ............... A61K 39/12; A61K 39/02; A61K 39/40; A61K 39/42; A61K 37/00; A61K 39/00

[52] U.S. Cl. ............... 424/86; 424/85; 424/87; 424/88; 424/89; 424/92; 424/93; 514/2; 514/21; 514/802; 530/364; 530/380; 530/381; 530/382; 530/383; 530/384; 530/386; 530/387; 530/389; 530/390; 530/392; 530/393; 530/397; 530/403; 530/404; 530/405; 530/408; 530/410; 530/806; 530/825; 530/826; 435/177; 435/188

[58] Field of Search ............ 424/85, 86, 87, 88, 424/89, 92, 93; 514/2, 21, 802; 530/364, 380, 381, 392, 383, 384, 386, 387, 389, 390, 392, 393, 394, 397, 403, 404, 405, 408, 410; 405/177, 188

[56] References Cited

U.S. PATENT DOCUMENTS

| | | | |
|---|---|---|---|
| 4,534,972 | 8/1985 | Lembach | 424/86 |
| 4,540,573 | 9/1985 | Neurath | 424/85 |
| 4,613,501 | 9/1986 | Horowitz | 424/89 |

OTHER PUBLICATIONS

D. O. White et al., Aust. J. Exp. Biol. Med. Sci., 41, 517 (1963).

V. D'Aurora et al., Biochem. Biophys. Res. Commun., 78(1), 170 (1977), 80 (4), 1025 (1978).

D. S. Sigman et al., J. Biol. Chem., 254(24), 12269 (1979).

K. M. Downey et al., Biochem. Biophys. Res. Commun., 93(1), 264 (1980).

D. Igdaloff et al., Biochem. Pharmacol., 32(1), 172 (1983).

K. Kariya et al., Biochem. Biophys. Res. Commun., 107(4), 1461 (1982).

W. R. Leopold et al., Cancer Res., 42, 4364 (1982).

N. Ackerman et al., J. Pharmacol. Exp. Ther., 215, 588 (1980).

I. L. Cartwright et al., Nucleic Acids Res., 10(19), 5835 (1982).

W. Levinson, Adv. Exp. Med. Biol., 91, 161 (1978).

S. Uesugi et al., "Deoxyoligonucleotide Chain Cleavage Reaction by Phenanthroline and Bleomycin", Nucleic Acids Symp., Sep. 1982; (11): 237–240.

R. Asano et al., "The Effect of Copper and Copper o-Phenanthroline Complex on Cattle Erythrocytes", Nippon Juigaku Zassi, Feb. 1983; 45 (1): 77–83.

B. Jessee et al., "Analogous Cleavage of DNA by Micrococcal Nuclease and A 1,10-Phenanthroline-Cuprous Complex", Nucleic Acids Res., Oct. 11, 1982; 10 (19):5823–34.

J. M. C. Gutteridge et al., "The Role of the Superoxide and Hydroxyl Radicals in the Degradation of DNA and Deoxyribose Induced by a Copper-Phenothroline Complex", Biochem. Pharmacol., Sep. 1, 1982, 31 (17): 2801–5.

L. M. Pope et al., "Products of DNA Cleavage by the 1,10-Phenanthroline-Copper Complex. Inhibitors of Escherichia Coli DNA Polymerase I", J. Biol. Chem., Oct. 25, 1982; 257 (20):12121–8 (Pope I).

C. Krishnamurti et al., "Effects of Ethylendiaminetetraacetic Acid and 1,10-Phenanthroline on Cell Proliferation and DNA Synthesis of Ehrlich Ascites Cells", Cancer Res., Nov. 1980: 40 (11):4092–9.

L. E. Marshall et al., "Cleavage of Deoxyribonucleic Acid by the 1,10-Phenanthroline-Cuprous Comples. Hydrogen Peroxide Requirement and Primary and Secondary Structure Specificity", Biochemistry, Jan. 20, 1981; 20 (2):244–50.

B. G. Que et al., "Degradation of Deoxyribonucleic Acid by a 1,10-Phenanthroline-Copper Complex. The Role of Hydroxyl Radicals", Biochemistry, Dec. 23, 1980; 19 (26):5987–91.

Y. Hiroshige, "The Effects of Copper and Copper o-Phenanthroline Complex on the Intact Human Erythrocytes", Tohoku J. Exp. Med., Apr. 1980; 130 (4): 385–402.

(List continued on next page.)

*Primary Examiner*—Howard E. Schain
*Attorney, Agent, or Firm*—James A. Giblin; Lester E. Johnson

[57] ABSTRACT

Compositions containing therapeutically or immunologically active proteins are rendered substantially free from infectious agents such as viable viruses and bacteria without substantial loss of therapeutic or immunologic activity by mixing the protein composition with a complex formed from transition metal ions, such as copper ions, and an angularly-fused, polynuclear heterocyclic arene having two nitrogen atoms in a "cis-ortho" relationship, such as phenanthroline, and a reducing agent such as a thiol or ascorbic acid or ascorbate salt or mixtures of ascorbic acid or ascorbate with a thiol in amounts and at a temperature and for a time sufficient to inactivate substantially all of the viruses and bacteria contained therein. Compositions containing therapeutically active proteins substantially free from viral and bacterial infectivity, which have heretofore been unattainable, can be prepared by the method of the invention.

24 Claims, No Drawings

OTHER PUBLICATIONS

K. T. Hiriyanni et al., "Purification and Properties of a DNA Polymerase from Mycobacterium Tuberculosis H37RV", Biochim. Biophys. Acta; 652:274–282, 1981.

D. R. Graham et al., "Cleavage of DNA by Coordination Complexes.

Superoxide Formation in the Oxidation of 1,10-Phenanthroline–Cuprous Complexes by Oxygen-Relevance to DNA Cleavage Reaction", J. Amer. Chem. Soc., 1980; 102, 5419–5421.

K. A. Reich et al., "Cleavage of DNA by the 1,10-Phenanthroline–Copper Ion Complex., Superoxide Mediates the Reaction Dependent on NADH and Hydrogen Peroxide", J. Amer. Chem. Soc., 1981, 103, 3582–3584.

L. A. Pope et al., "Secondary Structure Specificity of the Nuclease Activity of the 1,10-Phenanthroline–Copper Complex", Proc. Natl. Acad. Sci. USA, 81, 3–7 (1984). (Pope II).

PROTEIN COMPOSITIONS SUBSTANTIALLY FREE FROM INFECTIOUS AGENTS

CROSS-REFERENCE TO RELATED APPLICATION

This is a continuation-in-part of U.S. patent application Ser. No. 480,056, filed Mar. 29, 1983, now U.S. Pat. No. 4,534,972.

BACKGROUND OF THE INVENTION

1. Field of the Invention

This invention relates to and has among its objects novel compositions for therapeutic use and methods of making them. It is a particular object of this invention to provide compositions containing therapeutically active proteins which are substantially free from infectious agents such as viable viruses and bacteria, e.g. hepatitis viruses. Further objects of the invention will be evident from the following description wherein parts and percentages are by weight unless otherwise specified.

2. Description of the Prior Art

Many useful blood fractions and blood proteins are obtained from human blood plasma by fractionation according to known techniques such as, for example, the alcohol fractionation method of Cohn described in U.S. Pat. No. 2,390,074 (1945) and the *Journal of the American Chemical Society*, Vol. 68, page 459 (1946) and the Rivanol ®-ammonium sulfate method. The aforementioned methods as well as other variations and techniques are summarized in "The Plasma Proteins", second edition, Volume III, pages 548-550, Academic Press, New York, N.Y. (1977). These blood fractions contain biologically active proteins that possess certain therapeutic qualities. For instance, Factor VIII or antihemophilic factor is useful against hemophilia; plasminogen is a precursor of plasmin for treatment of acute thromboembolic disorders; immune serum globulin (IgG) is employed in the treatment of congenital gamma globulin deficiency, and prophylaxis of measles, poliomyelitis and hepatitis A and B; fibronectin has been implicated as active in treatment of burns, shock, cancer, etc.; antithrombin III is a coagulation inhibitor; cryoprecipitate itself may be used directly for classical hemophilia; Plasma Protein Fraction (human) and albumin are useful in treatment of shock due to burns, crushing injuries, abdominal emergencies, and any other cause producing a predominant loss of plasma fluids and not red cells; immune globulin, intravenous is a substitute for immune serum globulin administerable in larger quantities; Anti-inhibitor coagulant complex, or Factor VIII Inhibitor Bypassing Activity (FEIBA) described in U.S. Pat. No. 4,160,025 as a blood-coagulation-promoting preparation for Factor VIII inhibitor patients; alpha-1-proteinase inhibitor (alpha-1-antitrypsin) can be employed in the treatment of emphysema; plasma growth hormone corrects pituitary growth deficiency, somatomedin is useful in correcting growth deficiencies, other immune serum globulins, e.g., IgA, IgD, IgE, and IgM, may be employed to treat various immune protein deficiencies; prealbumin (U.S. Pat. No. 4,046,877) is employed to increase immunologic competence; plasminogen-streptokinase complex (U.S. Pat. No. 4,178,368) can be administered to patients for treatment of thromboembolisms; ceruloplasmin, transferrin, haptoglobin, and prekallikrein have reagent and other uses.

One problem confronting users of plasma, plasma fractions, and compositions containing individual blood proteins is the chemical and thermal instability of the therapeutically active proteins contained therein. In many cases, substantial, and sometimes complete, losses of activity are observed if these proteins are mixed with certain chemicals or heated above physiological temperatures, i.e., above about 40°-45° C. Consequently, these items require special care during preparation and storage to minimize such deactivation.

The chemical and thermal instability of the aforementioned proteins renders them difficult to free from viral and bacterial components. Therapeutically active proteins isolated from plasma may contain bacterial agents and viruses, e.g., hepatitis virus, present in the source material for the protein fraction, namely, blood from a donor. A risk of contracting hepatitis exists, therefore, for those receiving fractions from blood plasma fractionation because the presence of the virus cannot be detected with certainty by any known procedure. In a large number of situations, this risk is outweighed by the detriment to a patient in not receiving the therapeutic plasma fraction as determined by the physician.

Some therapeutically active proteins derives from plasma have been pasteurized, i.e. heated to reduce hepatitis infectivity successfully. For example, it is well known that albumin can be pasteurized by heating at 60° C. or 64° C. for 10 hours (Gellis et al., *J. Clin. Invest.*, Vol. 27, pages 239-244 (1948) in the presence of certain stabilizers such as N-acetyl-tryptophan and sodium caprylate. Individuals receiving this pasteurized material did not contract hepatitis, thus indicating the inactivation of hepatitis viruses while retaining the activity of albumin under the afore-described heating conditions. Plasma Protein Fraction (human) is also stabilized during pasteurization by the above method.

A process for pasteurizing the plasma protein plasminogen is disclosed by Baumgarten et al. in U.S. Pat. No. 3,227,626. An aqueous preparation containing 0.25-20 milligrams per milliliter (mg/ml) of plasminogen and further containing 0.1-0.5 molar lysine with a pH of 5.3-7.5 was heated at 60° C. for 10 hours. As the patentee states, hepatitis virus was destroyed and the danger of transmitting hepatitis was removed with retention of plasminogen activity. Attempts to pasteurize plasminogen under the above conditions in the absence of lysine resulted in complete destruction of plasminogen activity. It is interesting to note that plasminogen cannot be stabilized with N-acetyl-tryptophan and sodium caprylate during pasteurization, nor can albumin and Plasma Protein Fraction (human) be pasteurized in the presence of lysine.

Singher has described a process for treating plasminogen to produce a material that is not contaminated with hepatitis virus (U.S. Pat. No. 2,897,123). In the patented pasteurization technique, aqueous solutions of plasminogen are heated at about 60° C. for about 10 hours. The activity of plasminogen is retained if the solutions have a pH in the range not less than 3 nor greater then 6.5 and an ionic strength not greater than 0.3.

Another method for removing hepatitis virus from a biological material is described in U.S. Pat. No. 4,168,300. The material to be treated is contacted with a preparation, which may be agarose gel or beaded polyacrylamide plastic coupled with a variety of hydrophobic ligands. Plasma and albumin were subjected to the above purification technique to remove hepatitis virus.

Singher, in the aforementioned U.S. Pat. No. 2,897,123, lists some chemical and other types of methods of destroying hepatitis virus. The least effective of these methods involves the use of either nitrogen mustard or betapropiolactone. High energy irradiation in appropriate dosage is effective but destroys biological activity when applied to human blood products. Heat is recognized also as effective against hepatitis virus, the preferred treatment being heating the material at 60° C. for 10 hours. Higher temperatures above 70° C. for shorter intervals or lower temperatures for longer intervals have also been tried with successful results. However, it is important to note that higher temperatures are undesirable because of the potential for denaturation of the proteins. Furthermore, lower temperatures for long intervals are to be avoided because various proteolytic enzymes are activated under these conditions, and these activated enzymes cause protein degradation. Also, the use of temperatures lower than 60° C. for pasteurization has not been shown consistently to yield a material that does not contain the infective virus.

As mentioned above, the recognition that heating at 60° C. and 64° C. for 10 hours successfully destroys the hepatitis viruses in albumin was made by Gellis et al., supra. Gellis et al. proved experimentally that albumin heated under the above conditions did not transmit hepatitis even if hepatitis virus was present prior to pasteurization. However, the authors noted that hepatitis virus survived heating at 56° C. for one hour, a temperature usually employed for the inactivation of viruses. Thus, although heating at temperatures of about 56° C. for one hour will deactivate most viruses, hepatitis virus is not inactivated; and materials containing hepatitis virus, which are heated at 56° C. for one hour, cause infection of hepatitis in individuals receiving such materials.

Japanese Pat. No. 51-134878 (1976) teaches the stabilization of Factor XIII against heat inactivation (60° C. for 10 hours) by using 10-20% (w/v) of a stabilizer such as a neutral amino acid, a monosaccharide, or a sugar alcohol.

Furthermore, in U.S. Pat. No. 4,297,344 there is disclosed a method of stabilizing coagulation Factors II, VIII, XIII, antithrombin III and plasminogen against heat in the presence of 1-3 molar amount of a certain amino acid and 20-60% (w/w) of a carbohydrate.

In the production of pharmaceutical preparations such as virus vaccines, methods or means are necessary to inactivate or at least attenuate, the virus. The means or methods, on the one hand, must destroy or substantially reduce the infectiousness, but, on the other hand, must preserve the antigenic characteristics. Customary inactivation agents include, for example, Formalin, betapropiolactone, ethyl ethylenimine (U.S. Pat. No. 3,636,196), toluidine blue with irradiation, hydroxylamine, ethylene oxide (U.S. Pat. No. 3,456,053), and lower alkyl esters of acetic acid (U.S. Pat. No. 3,655,871).

It is known that a 2:1 1,10-phenanthroline-cuprous ion complex is a potent reversible inhibitor of isolated *E. coli* DNA polymerase I (D'Aurora et al., *Biochemical and Biophysical Research Communications*, Vol. 78, No. 1, pages 170-177, 1977). This complex has also been shown to be an effective inhibitor of isolated *E. coli* DNA dependent RNA polymerase, isolated *Micrococcus luteus* DNA dependent DNA polymerase, and isolated T4 DNA dependent DNA polymerase (D'Aurora et al., ibid., Vol. 80, No. 4, pages 1025-1032, 1978).

Sigman et al (*Journal of Biological Chemistry*, Volume 254, No. 24, pages 12269-12272, 1979) demonstrated that under aerobic conditions the cuprous-phenanthroline complex catalyzes depolymerization of poly (dA-dT) and relaxation of closed supercoiled SV40 DNA. In vitro inhibition of polymerase activity was related to such strand scission of the primer/template.

It is important in the treatment of a proteineous composition such as for example, a plasma protein composition containing viral and bacterial components or a virus vaccine, that the viral and bacterial infectivity of the composition be substantially reduced or eliminated while at the same time retaining a high yield of a substantial portion of the activity of the proteins in the protein composition or the antigenic activity of the virus vaccine. Many prior art methods do not allow the user to obtain all of the above objectives.

SUMMARY OF THE INVENTION

The invention described herein provides means for obviating the above-outlined problems. In the method of the invention certain compositions containing thermally and chemically sensitive, therapeutically active proteins are rendered substantially free from infectious agents such as viable viruses and bacteria by mixing the protein composition containing such infectious agents with a complex formed from a transition metal ion, such as copper ions, and an angularly-fused, polynuclear heterocyclic arene having at least two nitrogen atoms in a "cis-ortho" relationship, such as phenanthroline, and a reducing agent, such as a thiol or ascorbic acid or ascorbate group or mixtures thereof, in amounts and at a temperature and for a time sufficient to inactivate substantially all of the infectious agents contained therein without significant loss of the therapeutic activity of the protein. Alternatively, there may be used a complex formed from the reduced form of a transition metal ion, such as copper (I) ions, and the angularly-fused, polynuclear heterocyclic arene in combination with hydrogen peroxide, which may be added to the mixture or which may be generated in situ for example by enzymatic or chemical means. Compositions containing therapeutically active proteins heretofore unobtainable are available as a result of the process of this invention. Following the above treatment, the added agents are removed from the protein composition by conventional techniques, and the protein composition is processed according to conventional procedures for its ultimate therapeutic use.

The primary advantage of the invention is the availability of therapeutically active protein compositions, which heretofore have been unknown and unattainable. Since the therapeutically active protein compositions of the invention can be treated to render them substantially free from infectious agents with minimal loss of desirable activity, these valuable materials can be administered to patients, who can obtain the full therapeutic benefits thereof with a substantially reduced risk of being infected by a viral or bacterial agent.

Another advantage of the invention is that it may be applied to blood plasma prior to fractionation, to partially fractionated blood plasma, and to individual blood plasma fractions, as well as to individual blood plasma proteins themselves. Thus, the versatility of the present process can be seen.

Another advantage of the method of the invention is that it may be effective not only against hepatitis B virus but also against non A—non B hepatitis viruses.

Another advantage of the invention is that it may be used to inactivate viral or bacterial agents for preparation of vaccines.

A major advantage of the method of the invention is the substantial retention of desirable activity with substantial loss of viral and bacterial infectivity. This result is particularly surprising because of the chemical sensitivity of the proteins which are treated.

DESCRIPTION OF THE PREFERRED EMBODIMENTS

As mentioned above, the products of the invention include compositions comprising a thermally sensitive, therapeutically active protein substantially free from infectious agents such as viable viruses and bacteria. As mentioned above, a protein composition to be rendered substantially free from infectious agents is mixed with a complex formed from an angularly fused, polynuclear heterocyclic arene having two nitrogen atoms in a "cis-ortho" relationship, such as 1,10-phenanthroline, o-chrysoline, 5-methyl- or 5-chloro-1,10-phenanthroline and the like and a transition metal ion capable of complexing with the aforementioned arene such as ions of copper, and with a reducing agent selected from a thiol, for example, mercaptopropionic acid, mercaptoethanol, dithiothreitol and cysteine; ascorbic acid, ascorbate group present as an ester or as the anion component of an alkali or alkaline earth metal salt of ascorbic acid, a mixture of ascorbic acid or ascorbate with a thiol, NADPH, NADH, a mixture of NADPH or NADH with a thiol or ascorbic acid or ascorbate, and the like, said complex and reducing agent being used in amounts effective to inactivate substantially all of the infectious agents contained in said composition and which does not result in substantial loss of the therapeutic or immunologic activity. Hydrogen peroxide ($H_2O_2$) may optionally be added to control or minimize the concentration of reducing agent required for the virucidal effect, since the complexcatalyzed oxidation of the reducing agent generates $H_2O_2$ in the overall reaction.

Preferably the heterocyclic arene to be used according to the present invention has the following structure (Structural Formula A):

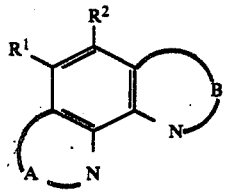

wherein $R^1$ and $R^2$, can be the same or different and represent hydrogen, $C_1$ to $C_4$ alkyl, $C_1$ to $C_4$ alkylcarbonyl such as succinyl, amino substituted $C_1$ to $C_4$ alkyl carbonyl such as glycyl, $C_1$ to $C_4$ alkoxy, halogen, $C_6$ to $C_{10}$ aryl or aralkyl groups, or together represent an annellated 5- to 7-membered ring, and A and B, which may be the same or different, represent 2- or 3-membered bridging groups, optionally containing nitrogen, oxygen or sulphur as a hetero atom and optionally being substituted with $C_1$ to $C_4$ alkoxy, halogen, $C_6$ to $C_{10}$ aryl or aralkyl groups and optionally containing annellated benzo groups, with the proviso that A and B, together with the nitrogen atoms, form aromatic rings and with the further proviso that the bridge members adjacent to the nitrogen atoms are unsubstituted.

More preferably, the heterocyclic arene to be used according to the present invention corresponds to the following formula (Structural Formula B):

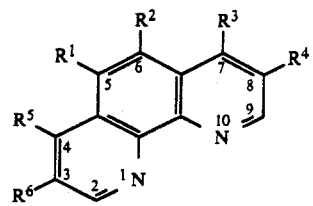

wherein $R^1$ and $R^2$ have the meaning indicated above and $R^3$ and $R^4$ and $R^5$ and $R^6$ may be the same or different and have the same meaning as $R^1$ and $R^2$.

Still more preferably, the radical $R^1$ to $R^6$ represent hydrogen, methyl or chlorine, or two adjacent radicals $R^1$ to $R^6$ represent an annellated benzene ring; most preferably, $R^1$ to $R^6$ all represent hydrogen.

The second component of the complex to be used according to the invention preferably is a salt of a transition metal ion which may exist in two oxidation levels such as copper, vanadium or cerium, copper ions being most preferred. Metal ion and reducing agent have to be selected in such a way that the complexed ion, when in its higher oxidation level, has the ability to be reduced by the reducing agent.

For the purpose of illustration, the following description will be directed to mixing of the protein composition to be treated with a complex formed from copper ions and 1,10-phenanthroline (ortho-phenanthroline) (Structural Formula B above wherein $R^1$ to $R^6$ are all hydrogen), and a reducing agent selected from 3-mercaptopropionic acid, ascorbic acid (sodium salt), and a mixture of 3-mercaptopropionic acid with ascorbic acid (sodium salt). This direction is not meant to provide a limitation on the invention, which includes within its scope all of the aforementioned agents.

In the method of the invention, the biological composition to be treated is suspended or dissolved in an aqueous medium and mixed with an aqueous solution of a complex formed from copper ions and 1,10-phenanthroline and a reducing agent in amounts and at a temperature and for a time sufficient to render it substantially free from infectious agents, that is, to render substantially all viruses and bacteria contained therein non-infective. The effective amounts of agents necessary to achieve the benefits in accordance with this invention depend on the type and concentration of proteins in the protein composition. Generally, however, a copper salt which provides copper ions and 1,10-phenanthroline are mixed together to give copper/1,10-phenanthroline complex (CuOP). When added to the protein composition the concentration of the CuOP complex should preferably be within the range of about $10^{-4}M$–$10^{-7}M$, more preferably about $10^{-4}M$–$10^{-6}M$, most preferably about $10^{-5}M$. The amount of total protein present in the biological protein composition may be in the range of from about 0.005% to about 10% (w/v) or more of protein. Typically, the total protein concentration will be in the range of about 0.01% to 8.0% (w/v). Preferably, the total protein concentration will be in the range of 0.5% to 4.0% (w/v). It is to be understood that when the biological protein composition is derived by means of biotechnology, e.g. genetic engineering, tissue culture or monoclonal antibody techniques, the amount or concentration of total protein will generally be at the lower amount of the typical range mentioned above. Thus, the CuOP complex may be prepared and added to the protein composition to be treated (or in a less preferred embodiment the above agents may be added to the protein composition and the complex prepared in situ).

The concentration of copper ion in the aqueous mixture of protein composition and complex is limiting and preferably should be in the range of about $10^{-4}$M (0.1 mM)–$10^{-7}$M (0.0001 mM), more preferably about $10^{-4}$ (0.1 mM)–$10^{-6}$M (0.001 mM), most preferably about $10^{-5}$M (0.01 mM). As the source of copper ions one may use the copper salts such as copper (II) sulfate, copper (II) acetate, copper (II) lactate, copper (II) nitrate.

Theoretically, the concentration of 1,10-phenanthroline (o-phenanthroline) required is twice the concentration of copper ion that is used. However, it has been found desirable to use an excess of 1,10-phenanthroline. A useful range of amount of 1,10-phenanthroline has been found to be about 0.05 mM–2 mM, more preferably about 0.1 mM–1 mM, most preferably about 0.5 mM. The use of a 50-fold excess of 1,10-phenanthroline (e.g. 0.5 mM) over copper ion (0.01 mM) has been found to be especially useful.

As mentioned above, the reducing agent used in the method according to this invention is selected from a thiol, ascorbic acid, ascorbate group present as an ester (e.g., a lower alkyl such as methyl or ethyl, an aryl such as phenyl, or aralkyl such as benzyl, ester) or as the anion component of an alkali metal (e.g. sodium or potassium) or alkaline earth metal (e.g. calcium or magnesium) salt of ascorbic acid, a mixture of ascorbic acid or ascorbate with a thiol (e.g. 3-mercaptopropionic acid, 3-mercaptoethanol, dithiothreitol, and cysteine), NADPH, NADH, and a mixture of NADPH or NADM with at least one of a thiol, ascorbic acid and ascorbate. Preferably, the reducing agent is a thiol, ascorbic acid, ascorbate group present as the anion component of an alkali or alkaline earth metal salt, or a mixture of ascorbic acid or ascorbate with a thiol.

It has been found that at least $10^{-M}$ (1 mM) of said reducing agent is required in the absence of added hydrogen peroxide and that there is no upper limit on the amount of reducing agent which may be used. The use of about 2–3 mM of reducing agent has been found to be advantageous in the method according to the invention. Although the use of amounts of reducing agent greater than 3 mM are effective to inactivate viruses and bacteria, such greater amounts have been observed to be associated with corresponding increasing loss of therapeutically active protein, for example antihemophilic factor (Factor VIII), activity. The reducing agent may be added to the aqueous mixture of protein composition and complex in a single addition or in sequential addition in proportions, for example in sequential proportions of 2 mM by 1 mM of reducing agent in the usual procedure. It is to be understood that amounts of reducing agent less than 1 mM may be required and will be useful when combined with the addition of hydrogen peroxide in the method.

After the above agents have been mixed with the protein composition, the mixture is held for a time and at a temperature sufficient to inactivate substantially all the viral and bacterial components of the protein composition while retaining a significant amount of the activity of the proteins therein. Viruses and bacteria are considered substantially non-infective for purposes of the invention when about 99% or more of the viral and bacterial infectivity has been eliminated. The therapeutically active protein is considered to have sufficient activity if it retains greater than about 70% of its activity.

The mixture of the protein composition and viral and bacterial inactivating agents is usually held at a temperature of about 2°–60° C., for a period from as little as one minute to several hours, e.g. about 3 or more hours. The time generally depends upon the rate of oxidation of the reducing agent. Preferably, the mixture is held at a temperature of about 20°–37° C., for a period of at least about 0.25 hours, more preferably about 0.5–3 hours.

The method of the invention is carried out usually under pH conditions that are compatible with the protein material being treated. Thus, the pH of the mixture should be within the range of about 4–10, preferably about 6–8, more preferably about 6.5–7.5. In general, pH conditions that insure the least disturbance to the active protein in the composition are desirable, where possible.

The effective amounts of a particular agent required to achieve the aforementioned objectives and the conditions necessary for achieving non-infectivity in accordance with the invention can be determined readily by one skilled in the art using pilot trials in accordance with the teaching contained herein.

Following treatment of the mixture as described above, the protein composition may be treated to remove the added agents including the added complex formed from the angularly-fused, polynuclear heterocyclic arene and the transition metal ion, low molecular weight reaction components (e.g. the reducing agent), and low molecular weight products of reaction components (e.g. derivatives of the reducing agents). Conventional techniques can be employed to achieve this end. For example, the mixture can be dialyzed or diafiltered using an appropriate semipermeable membrane. Other means of removing the agents will be suggested to those skilled in the art.

As mentioned above, the method of the invention may be applied to blood plasma prior to fractionation, to partially fractionated plasma, to individual plasma fractions, to individual plasma proteins isolated from plasma or from fractions thereof, and to products thereof. For example, in the production of antihemophilic factor concentrate starting from cryoprecipitate from human plasma using conventional precipitation technology employing precipitants such as polyethylene glycol (PEG), alcohol, aluminum hydroxide gel, or glycine and the like, the method of the invention may be applied to the solution or suspension of the cryoprecipitate or to a solution in the early stages or to the final solution just prior to removal of water to provide the final dried concentrate.

The protein composition then may be treated to remove water therefrom by procedures will known in the art. For instance, the mixture can be freeze-dried or ultrafiltered and then freeze-dried. Furthermore, the mixture can be sterile-filtered by conventional methods prior to water removal.

The protein compositions of the invention can be formulated into pharmaceutical preparations for therapeutic use. To prepare it for intravenous administration the protein composition is dissolved usually in water containing physiological substances such as sodium chloride, glycine, and the like and having a buffered pH compatible with physiological conditions. Generally, guidelines for intravenously administered protein compositions are established by governmental regulation.

Thermally and chemically sensitive, therapeutically active proteins included within the scope of the invention are those proteins generally administered to patients for preventative and/or curative purposes which lose some therapeutic activity when heated above about 40°–45° C. or in the presence of certain chemicals. Examples of therapeutically active proteins that may be treated in accordance with the present invention, by way of illustration and not limitation, are those proteins derived from venous blood plasma or placental plasma and include blood plasma, partially fractionated blood plasma, individual blood plasma fractions, and individual blood plasma proteins. Thus, for example, protein compositions which may be treated by the method of the invention include the therapeutically active protein plasminogen, albumin, antihemophilic factor (Factor VIII), Factor IX concentrate containing Factors II and VII and IX and X, Factor II, Factor VII, Factor IX, Factor X, Plasma Protein Fraction (human), fibronectin (cold insoluble globulin), Factor XIII, an immune serum globulin such as IgG, IgA, IgD, IgE, and IgM, high molecule weight kininogen (90,000–106,000 daltons), an immune globulin, intravenous (modified, either chemically or enzymatically or by fractional separation) immune serum globulin, monoclonal antibodies, FEIBA, antithrombin III, alpha-1-proteinase inhibitor, plasma proteins having physiologic activity, such a plasma growth hormone, somatomedin, prealbumin, plasminogen-streptokinase complex, ceruloplasmin, transferrin, haptoglobin, and prekallikrein, etc., and mixtures thereof. In addition, compositions containing "defatted" albumin and "defatted" Plasma Protein Fraction (human), i.e., PPF (human), are available through the invention. The term "defatted" means that the albumin and PPF (human) contain no more fatty acid material than that present in the native state prior to treatment. The treated defatted compositions can be administered to patients who cannot tolerate infusion of high fatty acid material such as that obtained using standard pasteurization stabilizing agents, namely, sodium caprylate and N-acetyl-tryptophan.

Examples of viral vaccines or non-infectious antigens that may be attained in accordance with the teachings outlined herein are hepatitis B virus, equine influenza types A1 and A2, vesicular stomatitis virus, and so forth. A virus which has been inactivated according to the Examples below may be used in the preparation of a vaccine according to known procedures. A description of such vaccine production may be found in "Development and Chimpanzee Testing of a Vaccine Against Human Hepatitis B", E. B. Buynalz et al, *Proc. Soc. Exp. Bio & Med.*, 151:694–700 (1976), which is hereby incorporated by reference.

The term therapeutically active protein herein is intended broadly to include, for example, blood plasma proteins (therapeutic) as listed above and virus or bacterial vaccines or non-infectious antigens (immunologic) and other such proteins which are useful in treating or preventing a biological or physical disorder which includes also those proteins produced by means of biotechnology, e.g., genetic engineering, tissue culture or monoclonal antibody techniques. Generally, such therapeutically active proteins would also be chemically or thermally sensitive.

In order to ensure the non-infectivity of compositions of protein produced by means of biotechnology using protein-producing organisms in a suitable medium, the method of this invention can be used to inactivate such organisms, and/or adventitious infectious agents, such as viable viruses, and/or nucleic acid genetic material from such organisms or adventitious agents by contacting the protein-producing organisms, extracts thereof, and culture media containing nucleic acid genetic material, the mixture of the organisms and medium, and the adventitious infectious agents which may be associated with any of the above, with an aqueous solution of the heterocyclic arene-transition metal complex in the presence of a reducing agent thus causing the breakdown of nucleic acid genetic material, whether contained in the intact organism or associated with adventitious infectious agents or released into the medium during growth, lysis or processing. The resulting compositions so treated would be substantially safer and more desirable for further processing of the biotechnology product.

The compositions of the invention comprise a protein selected from the group consisting of components of blood plasma, viral or bacterial vaccines, and non-infectious antigens characterized by being substantially therapeutically or immunologically active and substantially free from infectious agents. The present compositions should have substantially undiminished antigenic character when compared to such compositions which have been subjected to other chemical treatment to inactivate viral or bacterial components.

The compositions of the invention should also be substantially unchanged in monomeric form when compared to such compositions which have been heat treated to render them free of viral and bacterial components.

As mentioned above the products of the invention may be incorporated into pharmaceutical preparations, which may be used for therapeutic purposes. However, the term "pharmaceutical preparation" is intended in a broader sense herein to include preparations containing a protein composition treated in accordance with this invention used not only for therapeutic purposes, but also for reagent and diagnostic purposes as known in the art; for tissue culture wherein organisms such as viruses for the production of vaccines, interferon, and the like, are grown on plasma or on plasma fractions, e.g., Cohn Effluent II+III, Cohn Fraction IV, Cohn Fraction V, and so forth; etc.

For any of the above uses it is advantageous that the protein composition be free of infective hepatitis and other viruses or bacteria as provided in the instant invention. The pharmaceutical preparation intended for therapeutic use should contain a therapeutic amount of a protein composition treated in accordance with the invention, i.e., that amount necessary for preventative or curvative health measures. If the pharmaceutical preparation is to be employed as a reagent, then it should contain reagent amounts of protein composition. Similarly, when used in tissue culture or a culture medium the protein composition should contain an amount of protein composition sufficient to obtain the desired physiologic effect. It should be obvious that protein compositions treated in accordance with this invention will not contain infective amounts of viruses and other organisms which are inactivated under the conditions described.

EXAMPLES

The invention is demonstrated further by the following illustrative examples.

Assay Methods

Factors II and VII: Factor II and Factor VII were assayed by the method of Owren described in the *Scand. J. Clin. and Lab. Investigation*, Vol. 1, page 81 (1949).

Factors X and Xa: Factor X and Factor Xa were assayed by the method of Bachmann et al, described in *Thromb. Diath. Haemorrh.*, Vol. 2, page 24, (1958).

Thrombin: The assay procedure employed was described by Fenton II et al, in *Thrombosis Res.*, Vol. 4, pages 809–817 (1974).

Factors IX and VIII: Modification of the procedures described by Langdell et al (partial thromboplastin time technique), *J. Lab. Clin. Med.*, Vol. 41, pages 637–647 (1953) and by Proctor et al (kaolin clotting time method) *Amer. J. Clin. Path.*, Vol. 36, page 212 (1961) were employed. Platelet Factor 3 was supplied by a cephalin suspension. Maximum surface contact activation was achieved with Celite ® powder. All other clotting factors (except Factor IX or Factor VIII) were supplied by a substrate comprising plasma from a patient severely deficient in Factor IX or Factor VIII mixed with barium sulfate adsorbed beef plasma. Quantitation of an unknown specimen was made by comparing its clotting time in the test with that achieved by dilutions of a normal standard.

The exact assay procedure is the same for both Factor IX and Factor VIII except that the activator in Factor IX assay is Platelin ® Plus Activator instead of automated APPT reagent (General Diagnostics, Inc., Morris Plains, N.J.).

Alpha-1-proteinase Inhibitor (PI): PI is estimated by its elastase inhibitory capacity, using a chromogenic substrate for elastase. Hydrolysis of N-succinyl-L-alanyl-L-alanyl-L-alanyl-p-nitroanilide (SA$_3$pNA) by elastase causes an increase in absorption at 405 nm. This increase is continuously monitored usually at 37° C. Comparisons of the linear changes of absorbance with time in the presence and absence of sample (PI) are made. The amount of inhibitor is then calculated based on the known molecular weights of elastase and PI, on the known 1:1 stoichiometry, and on the known amount of elastase used.

Hepatitis B Virus DNA Polymerase: The assay procedure employed was described by Hirschman and Garfinkel, in *J. Infect. Dis.*, Vol. 135, pages 897–910 (1977).

EXAMPLE 1

A. A commercial Factor IX concentrate (Konyne ®, Cutter Laboratories, Inc.) containing Factors II, VII, IX and X (0.5 ml.) was mixed with 0.5 ml. of 0.025M (TRIS) buffer (pH 7.5) containing a copper/1,10-phenanthroline complex formed by adding to the buffer 1,10-phenanthroline to a concentration of $1.0 \times 10^{-3}$M and copper II sulfate (CuSO$_4$) to a concentration of $2 \times 10^{-5}$M. Next, 3-mercaptopropionic acid (MPA) was added to the mixture to a final concentration of $0.5 \times 10^{-3}$M. The total protein content of the resulting mixture was 1%. The mixture was heated at 37° C. for 20 minutes.

Factor II, VII, IX, and X activities of the treated material were determined using the aforementioned assays. Less than 20% of the Factor IX activity was lost during the above treatment. Furthermore, no significant loss of activity for Factors II, VII, and X was observed under these conditions.

B. Dane particles were isolated from Hepatitis B Surface Antigen (HBsAg)-positive human plasma by differential centrifugation and were purified by sedimentation through sucrose. The purified particles were precipitated by anti-HBsAg and contained endogenous DNA polymerase activity which was augmented by treatment with non-ionic detergents. Commercial Factor IX concentrate (Konyne ®) was inoculated with an aliquot of the above preparation sufficient to provide 2000 to 3000 cpm in the polymerase assay ($^3$H-deoxynucleotide incorporation into DNA), and the suspension was mixed with Tris Buffer containing CuSO$_4$ and 1,10-phenanthroline (final concentrations: 0.025M Tris-HCl, $0.5 \times 10^{-3}$M 1,10-phenanthroline, $1 \times 10^{-5}$M CuSO$_4$, 1% total protein). MPA was added (0, 0.5, 1, 2 and 5 mM final concentration) and the suspensions were incubated at 37° C. for 20 minutes, prior to addition of a $^3$H-deoxynucleotide mixture for analysis of DNA polymerase activity. In the absence of reducing agent, less than 10% loss of DNA polymerase activity was observed while at concentrations of MPA of 1 mM or greater, approximately 95% inactivation was achieved. With 0.5 mM MPA, approximately 90% loss of polymerase activity occurred.

C. Dane particles were isolated as described in Example 1B and core particles were prepared by exposure to 1% (v/v) Triton X-100. The particles were incubated with H-deoxynucleotides to label the DNA through the action of the endogenous DNA polymerase, and were then isolated by chromatography on Sepharose CL-6B. The labeled particles were treated with cuprous-phenanthroline complex as described in Example 1B, the reaction was terminated with EDTA, and the particles were disrupted by heating with 2% sodium dodecylsulfate (60° C., 20 min.). Controls were treated in the same way, without addition of the complex. Samples were heated to 100° C. for 10 min., quenched rapidly in an ice-salt bath, and were analyzed by density gradient centrifugation (6–20% [w/w] sucrose, 0.01M Tris-Cl, pH 7.5, 0.001M EDTA; 34,000 RPM, 20 hours, 18° C.). Fractions were collected and acid-precipitable cpm were determined. Control and treated samples each exhibited a single major radioactive peak. The DNA in the control preparation had an S-value approximately 3 to 5 times that obtained following CuOP treatment of the core particle, indicative of extensive degradation induced by the complex.

EXAMPLE 2

A commercial Factor VIII preparation (Koate ® from Cutter Laboratories, Inc.) was treated with copper phenanthroline under conditions similar to those described in Example 1A (final concentration of $0.5 \times 10^{-3}$M 1,10-phenanthroline, $1 \times 10^{-5}$M CuSO$_4$, $2 \times 10^{-3}$M 3-mercaptopropionic acid, 1% total protein, 30 minutes, 37° C.), and Factor VIII activity was measured by standard coagulation assay. No loss of Factor VIII activity was observed. Similar results were obtained following treatment for 150 minutes under the same conditions.

EXAMPLE 3

Alpha-1-proteinase inhibitor (PI) was prepared as follows: Fraction IV-1 was obtained from human plasma by means of Cohn fractionation. Fraction IV-1 paste (10.0 g) was dissolved in 0.1 liter of a buffer solution of pH 8.5 containing 0.1M (TRIS) and 0.02M sodium chloride. The mixture was stirred for 16 hours at 5° C. PEG 4000 (from Union Carbide Corporation) was added to a level of 14% (w/v). The mixture was stirred to dissolve the PEG and then centrifuged at 15,000×g. The supernatant was collected, diluted with 0.22 volumes of water, acidified to pH 5.1 by addition of 1N acetic acid, and centrifuged. The supernatant containing the PI was collected and concentrated.

The above preparation was treated with copper phenanthroline under conditions described in Example 2. No loss of PI activity occurred under these conditions.

EXAMPLE 4

Vesicular Stomatitis Virus (VSV) R. Roby, Cutter Laboratories, Inc.) was added to Eagle's Minimal Essential Medium (EMEM) from Grand Island Biological Company containing 0.01M Tris-HCl (pH 7.5), $1 \times 10^{-5}$M CuSO$_4$, and $0.5 \times 10^{-3}$M 1,10-phenanthroline. After the addition of 3-mercaptopropionic acid (MPA, previously neutralized with NaOH) to a final concentration of $0.5 \times 10^{-3}$M, the viral suspension was incubated at 37° C. for 20 minutes. Controls included virus incubated in Tris-buffered EMEM as indicated above, but without the addition of MPA. Following the incubation, the virus suspensions were serially diluted and adsorbed to confluent monolayers of HeLa cells for 60 minutes at 37° C. The cultures were washed with calcium- and magnesium-free phosphate buffered saline, overlaid with EMEM containing 10% fetal calf serum and 0.5% agarose, and incubated at 37° C. for two to three days in a humidified CO$_2$ incubator prior to enumeration of plaques. Virus titer was found to decrease from $2.1 \times 10^7$ plaque forming units (PFU)/ml to $3 \times 10^2$ PFU/ml following exposure to copper-phenanthroline complex in the presence of reducing agent. Treatment with copper-phenanthroline complex alone, in the absence of reducing agent, had a minimal effect on the virus titer ($1.3 \times 10^7$ PFU/ml).

EXAMPLE 5

Two strains of Equine Influenza virus were utilized in these experiments. The A1 strain was Pennsylvania which had been grown in tissue culture to $10^{8.4}$ virus particles/ml. The A2 strain was Miami which had been grown in tissue culture to $10^{8.3}$ or $10^{9.2}$ virus particles/ml. The test protocol was the same in each inactivation study. Virus inactivation was determined by titration of control virus or treated virus in 9-day old embryonated chicken eggs. The procedure employed was as follows:

Components: 0.5M Tris Buffer pH 7.5; 0.1 mM CuSO$_4$; 10 mM o-phenanthroline; 10 mM Mercaptopropionic Acid neutralized with NaOH. All solutions were filter sterilized through 0.2μ filters.

Test System: The following components were added in order of listing.

| Test | | Control |
|---|---|---|
| 6.8 ml | Sterile H$_2$O | 8.8 ml |
| 0.2 ml | TRIS .5 M pH 7.5 | 0.2 ml |
| 1.0 ml | 0.1 mM CuSO$_4$ | — |
| 0.5 ml | 10 mM o-Phenanthroline | — |
| 1.0 ml | Virus | 1.0 ml |
| 0.5 ml | 10 mM MPA | — |

Total Volume was 10.0 ml. The initial virus titer was the same as a 1:10 dilution of the original virus preparation. Control and test vials were incubated at 37° C. (Miami) or 5° C. (Pennsylvania).

Titration Procedure: A 0.5 ml sample was removed from the control vial as soon as possible. This was considered the 0-time sample. Further 0.5 ml samples were removed from control or test vials at 5 min., 30 min., 60 min., or 180 min. as indicated. 0.5 ml samples were serially diluted in 10-fold increments through $10^{-9}$. Dilution blanks consisted of 0.01M Phosphate Buffered Saline plus 0.2% Bovine Serum Albumin. 1.0 ml was removed from each dilution vial and injected via a 1.0 cc tuberculin (TB) syringe and 23 ga ⅝" needle into 5 embryonated chicken eggs (0.2 ml/egg). After injection of all the eggs the holes where the needle penetrated the egg was sealed using collodion. Eggs were incubated at 34° C. for 72 hours to allow virus growth. Eggs were then placed at 5° C. for 24 hours to kill the embryo after which the egg was opened and 0.5 ml of amniotic fluid was removed and tested for presence of virus by hemagglutination of Red blood cells (chicken). Results are shown as the number of eggs showing positive (hemagglutination indicating presence of virus) compared with the number of total eggs inoculated with that dilution. Titers are calculated using the method of Reed and Muench. (Am. J. Hygiene 27, 493 [1938]).

Results Showing Inactivation by o-Phenanthroline: Miami Lot 136 was totally inactivated from a titer level of $10^{8.2}$ virus particles/ml after 3 hours at 37° C.

Miami Lot 137 was totally inactivated by 30–60 min. at 37° C. from a titer level of $10^{7.3}$ virus particles/ml.

Pennsylvania strain requires between 30 min. and 60 min. for total inactivation at 5° C. from a titer level of $10^{7.5}$ virus particles/ml.

EXAMPLE 6

The inactivation of Neurovaccina Virus, Murine Cytomegalovirus and Lymphocytic Choriomenigitis Virus was evaluated in a similar way to that described in Example 5, using appropriate methods for virus quantitation.

The results for Neurovaccinia Virus demonstrated rapid and complete inactivation from a titer level of $10^5$ virus particles/ml.

Murine Cytomegalovirus was completely inactivated after 60 minutes incubation at 37° C. from a titer level of $10^4$ virus particles/ml.

The results for Lymphocytic Choriomeningitis Virus indicated complete inactivation in 60 minutes from a titer level of $10^7$ virus particles/ml.

EXAMPLE 7

E. coli (ATCC No. 23503) was grown to log phase, harvested and washed once by centrifugation, and resuspended in phosphate buffered saline at approximately $10^9$ organisms/ml. Cupric sulfate ($1 \times 10^{-5}$M), o-phenanthroline (0.5 mM), and sodium mercaptopropionate (0.5 mM) were added sequentially to the indicated final concentrations and the suspension was incubated at 37° C. with rotation (100 r.p.m.). Aliquots were removed at intervals and diluted for plating. Colonies were enumerated at 24, 48 and 72 hours; all three counts were identical.

The *E. coli was inactivated to a extent greater than 99%* after 30 min. from a titer of $10^9$ colony forming units/ml.

EXAMPLE 8

The effect of copper phenanthroline treatment on the prothrombin activity curve of normal pooled plasma was measured by standard coagulation techniques. During one hour of treatment at 37° C., under conditions described in Example 1A, there was no effect of copper phenanthroline on this measure of the overall extrinsic pathway of blood coagulation.

EXAMPLE 9

Human adenovirus-2 was treated with copper phenanthroline as described in Example 1A. DNA was isolated and subjected to agarose electrophoresis. Extensive and heterogeneous degradation of DNA was observed.

EXAMPLE 10

Vesicular stomatitis virus (an RNA-containing virus) was added to a solution of Factor VIII concentrate (a complex protein composition prepared from human plasma) containing 0.05M Tris-HCl (pH 7.5), $1 \times 10^{-5}$M $CuSO_4$ and $0.5 \times 10^{-3}$M 1,10-phenanthroline. 3-Mercaptopropionic acid (sodium salt) or ascorbic acid (sodium salt), independently, was then added to duplicate samples of the protein composition to a final concentration of 3 mM and the resulting mixtures were incubated at room temperature for 40 minutes with stirring. Control samples were incubated under the same conditions without the addition of 3-mercaptopropionic acid or ascorbic acid. Residual virus was assayed as described in Example 4 by adsorption of appropriate dilutions of the reaction mixtures to confluent monolayer cultures of HeLa cells and enumeration of virus plaques following two to three days incubation at 37° in a humidified $CO_2$ incubator. Virus titer was found to decrease from $2.9 \times 10^7$ plaque forming units (PFU)/ml to $<10^2$ PFU/ml (detection limit of assay) following exposure to copper phenanthroline complex in the presence, independently, of 3-mercaptopropionic acid or ascorbic acid.

EXAMPLE 11

Vaccinia virus (a DNA-containing virus) was added to a solution of Factor VIII concentrate and the suspension was treated with copper phenanthroline complex in the presence of 3 mM 3-mercaptopropionic acid (sodium salt) and 3 mM ascorbic acid (sodium salt), independently, under the same conditions described in Example 10. Residual virus was assayed by measuring the cytopathic effect observed in confluent cultures of MRC-5 human fibroblasts exposed to appropriate dilutions of the reaction mixtures for one week at 37° in a humidified $CO_2$ incubator. Vaccinia virus was completely inactivated from an initial titer of greater than $1 \times 10^5$ particles/ml following treatment with copper phenanthroline complex in the presence, independently, of 3-mercaptopropionic acid or ascorbic acid.

EXAMPLE 12

High titer vesicular stomatitis virus was added to a solution of Factor VIII concentrate containing 10 mM imidazole, 20 mM histidine, 100 mM ammonium formate, pH 7.0, $1 \times 10^{-5}$M $CuSO_4$ and 0.5 mM 1,10-phenanthroline. Reducing agent was added to the reaction mixture as indicated below, and after 30 minutes incubation at room temperature, residual virus titer was determined as outlined in Example 10, with the following results:

| Reducing Agent | Residual Titer |
| --- | --- |
| None | $2.0 \times 10^9$ |
| 2 mM 3-Mercaptopropionic acid (3-MPA) | $1.8 \times 10^4$ |
| 2 mM Cysteine | $2.6 \times 10^5$ |
| 2 mM 3-MPA + 1 mM Ascorbic acid | $<10^2$ |
| 2 mM Cysteine + 1 mM Ascorbic acid | $<10^2$ |
| 3 mM 3-MPA | $2.2 \times 10^4$ |
| 3 mM Cysteine | $3.8 \times 10^3$ |
| 3 mM Ascorbic acid | $2.9 \times 10^4$ |

The combination of copper phenanthroline complex with either cysteine or mercaptopropionic acid or ascorbic acid was found to induce a highly significant inactivation of virus. When either cysteine or 3-mercaptopropionic acid was present in combination with ascorbic acid in the reaction mixture, virus kill was greater than that attained when either reducing agent was used alone at comparable concentrations.

EXAMPLE 13

Solubilized cryoprecipitate (total protein concentration approximately 4%) from human plasma, the starting material for preparation of Factor VIII concentrate, was treated with copper phenanthroline complex plus reducing agent(s) under the same conditions described in Example 12. Factor VIII activity was measured after 60 minutes treatment at room temperature. There was no significant loss of Factor VIII activity using any of the reducing agents described in Example 12. Substantial virus inactivation, dependent on the nature of the reducing agent as in Example 12, was observed in parallel samples of solubilized cryoprecipitate previously inoculated with Vesicular Stomatitis Virus (starting titer = $1.7 \times 10^9$) and similarly treated with copper phenanthroline complex.

EXAMPLE 14

A solution of Factor VIII concentrate was treated with copper phenanthroline complex plus reducing agent under the same conditions described in Example 12. There was no significant loss of Factor VIII activity under any of the conditions.

EXAMPLE 15

A solubilized protein fraction obtained from human plasma and containing high levels of Factor IX activity was treated at pH 7.0 with copper phenanthroline complex plus the combination of 1 mM ascorbic acid/2 mM 3-mercaptopropionic acid under the conditions described in Example 12. Factor IX activity was subsequently purified further by standard chromatographic techniques. No significant loss of Factor IX activity was observed and the purified Factor IX was in all respects indistinguishable from the material obtained without exposure to copper phenanthroline complex.

EXAMPLE 16

Supernatant fluids obtained from cultures of Epstein-Barr virus (EBV)-transformed human B lymphoblastoid cells and containing monoclonal antibody (IgM) of defined antigenic specificity were treated with copper phenanthroline complex plus reducing agent under the conditions described in Example 12. No changes in structure were detected by chromatographic or electrophoretic analysis of antibody isolated following this treatment. In addition, binding to specific antigen was retained in the copper phenanthroline treated antibody. Epstein-Barr virus in culture supernatants obtained from the marmoset cell line B95-8 was found to be completely inactivated by exposure to copper phenanthroline complex plus reducing agent under these conditions. The virus was assayed by its ability to transform human B cells.

EXAMPLE 17

This Example illustrates the contemplated use of the method according to this invention to degrade and render innocuous nucleic acids and/or nucleoproteins contained in supernatant fluids and other product compositions obtained using biotechnology techniques.

Supernatant fluids obtained from cultures of EBV-transformed human B-lymphoblastoid cells, or of hybridomas producing therapeutically active or diagnostically useful monoclonal antibodies, or mammalian cells or other organisms containing and expressing the genetic information coding for therapeutically active proteins (e.g. Factor VIII, Factor IX, alpha-1-proteinase inhibitor, antithrombin-III and the like), such information being inserted into the cellular genome by genetic engineering techniques, are treated with copper phenanthroline complex plus reducing agent under the conditions described in Example 12. Nucleic acids are isolated from these supernatant fluids using standard phenol-chloroform extraction techniques (e.g., Penman, S., *Fundamental Techniques in Virology* (K. Habel and N. P. Salsman, eds.), Academic Press, N.Y., 1969, pp. 35-48). The size distribution of the isolated nucleic acids is determined by agarose electrophoresis or size exclusion chromatography and compared with that observed in control preparations obtained from duplicate aliquots of supernatant fluids not treated with copper phenanthroline complex plus reducing agent.

EXAMPLE 18

In order to evaluate removal of 1,10-phenanthroline and other low molecular weight reaction components from protein products exposed to copper phenanthroline complex in the presence of a reducing agent, solubilized Factor VIII concentrate (protein concentration≈1.5% w/v) was treated with copper 2,3,4,7,8,9-$^{14}$C-1,10-phenanthroline plus 2-3 mM 3-mercaptopropionic acid as described in Example 12. After the reaction was completed, the reaction mixture was either dialyzed or diafiltered using an appropriate semi-permeable membrane, or was subjected to gel permeation chromatography. As anticipated for a low molecular weight compound, 1,10-phenanthroline was readily separated from proteins by either dialysis or diafiltration. Gel permeation chromatography was found to decrease the residual concentration of phenanthroline in the treated protein solutions to levels below the limit of detection of the isotopic methods employed. Like removal of other low molecular weight reaction components and products by dialysis, diafiltration, or gel permeation chromatography, or other similar methods, would be anticipated on the basis of these results. There was no significant loss of Factor VIII activity after removal of 1,10-phenanthroline by these methods.

What is claimed is:

1. A method for rendering a composition, which contains a therapeutically or immunologically active protein, selected from the group consisting of blood plasma proteins, virus vaccines, bacterial vaccines, and non-infectious antigens dissolved in an aqueous medium, substantially free from infectious agents selected from viable viruses and bacteria without substantial loss of therapeutic or immunologic activity, which comprises (a) mixing an aqueous solution of the protein composition with an effective amount of a complex formed from mixing an angularly-fused, polynuclear heterocyclic arene having two nitrogen atoms in a "cis-ortho" relationship and a transition metal ion capable of complexing with said arene and a reducing agent, selected from ascorbic acid, ascorbate group present as an ester or as the anion component of an alkali metal or alkaline earth metal salt of ascorbic acid, a mixture of ascorbic acid or ascorbate with a thiol, NADPH, NADH, and a mixture of NADPH or NADH with at least one of a thiol, ascorbic acid and ascorbate in an effective amount, said amounts being effective to inactivate substantially all of the infectious agents contained in said composition and which does not result in substantial loss of thereapeutic or immunologic activity, and (b) holding the mixture for a time and at a temperature sufficient to render said infectious agents substantially non-infective in the protein composition without substantial loss of therapeutic or immunologic activity therein.

2. The method of claim 1 wherein the mixture is held in step (b) at a temperature of about 2°-60° C. for a period of at least about 1 minute.

3. The method of claim 1 wherein the mixture is held in step (b) at a temperature of about 20°-37° C. for a period of at least about 0.25 hours.

4. The method of claim 1 wherein the mixture is held for a time and at a temperature to inactivate at least about 99% of the viruses and bacteria in the protein composition.

5. The method of claim 1 wherein the pH in step (b) is physiologically compatible.

6. The method of claim 1 wherein the pH is about 4-10.

7. The method of claim 1 wherein the amount of complex in step (a) is about 0.0001-0.1 mM in an aqueous solution containing about 0.005-10% (weight/volume) of the protein composition.

8. The method of claim 1 wherein the amount of reducing agent is at least about 1 mM in the absence of added hydrogen peroxide in an aqueous solution containing about 0.005-10% (weight/volume) of the protein composition.

9. The method of claim 1 wherein the complex is a copper/1,10-phenanthroline complex.

10. The method of claim 1 wherein the reducing agent is selected from (a) ascorbic acid, (b) ascorbate group present as the anion component of one of an alkali metal and an alkaline earth metal salt, and (c) a mixture of one of ascorbic acid and ascorbate group present as the anion component of one of an alkali metal and an alkaline earth metal salt with a thiol.

11. The method of claim 1 wherein the reducing agent is a mixture of one of ascorbic acid and ascorbate group present as the anion component of one of an alkali metal and an alkaline earth metal salt with a thiol.

12. The method of claim 1 wherein the reducing agent is a mixture of one of cysteine and 3-mercaptopropionic acid with ascorbic acid (sodium salt).

13. The method of claim 1 including the further step of:
   (c) removing the added complex formed from the angularly-fused, polynuclear heterocyclic arene and the transition metal ion, low molecular weight reaction components, and low molecular weight products of reaction components.

14. The method of claim 13 wherein the protein composition comprises a component derived from blood plasma.

15. The method of claim 13 wherein the protein composition comprises a viral vaccine.

16. The method of claim 13 wherein the protein composition comprises non-infectious antigen.

17. The method of claim 13 wherein the protein composition comprises a protein selected from the group consisting of blood plasma, partially fractionated blood plasma, plasminogen, albumin, antihemophilic factor (Factor VIII), Factor IX concentrate containing Factors II and VII and IX and X, Factor II, Factor VII, Factor IX, Factor X, Plasma Protein Fraction (human), fibronectin (cold insoluble globulin), Factor XIII, IgG, IgA, IgD, IgE, IgM, high molecular weight kininogen (90,000-106,000), an immune globulin, intravenous (modified, either chemically or enzymatically or by fractional separation) immune serum globulin, monoclonal antibodies, anti-inhibitor coagulant complex (FEIBA), antithrombin III, alpha-1-proteinase inhibitor, plasma growth hormone, somatomedin, prealbumin, plasminogen-streptokinase complex, ceruloplasmin, transferrin, haptoglobin, and prekallikrein and mixtures thereof.

18. A product produced by the method of claim 14.
19. A product produced by the method of claim 15.
20. A product produced by the method of claim 16.
21. A product produced by the method of claim 17.
22. A method for rendering non-infective and innocuous, without substantial loss of activity, a composition which contains a protein produced by means of biotechnology by protein-producing organisms in a suitable medium which comprises
   (a) contacting said medium containing at least one of (i) intact protein-producing organisms, and (ii) adventitious agents such as viruses, and (iii) nucleic acid genetic material from the protein-producing organisms or adventitious agents with an aqueous solution of an effective amount of a complex formed from mixing an angularly-fused, polynuclear heterocyclic arene having two nitrogen atoms in a "cis-ortho" relationship and a transition metal ion capable of complexing with said arene and a reducing agent, selected from a thiol, ascorbic acid, ascorbate group present as an ester or as the anion component of an alkali metal or alkaline earth metal salt of ascorbic acid, a mixture of ascorbic acid or ascorbate with a thiol, NADPH, NADH, and a mixture of NADPH or NADH with at least one of a thiol, ascorbic acid and ascorbate in an effective amount, said amounts being effective to inactivate substantially all of the infectious agents contained in said composition and which does not result in substantial loss of activity of the protein, and
   (b) holding the mixture from Step (a) for a time and at a temperature sufficient to render said protein-producing organisms, adventitious agents, and nucleic acid genetic material from said protein-producing organisms and adventitious agents substantially non-infective and innocuous without substantial loss of protein activity.

23. The method of claim 22 including the further step of:
   (c) removing the added complex formed from the angularly-fused, polynuclear heterocyclic arene and the transition metal ion, low molecular weight reaction components, and low molecular weight products of reaction components.

24. A product produced by the method of claim 23.

* * * * *